(12) United States Patent
Li et al.

(10) Patent No.: US 8,349,811 B2
(45) Date of Patent: Jan. 8, 2013

(54) STABLE 6-METHOXY-2',3'-DIDEOXYGUANOSINE, METHOD FOR PREPARING THE SAME AND PHARMACEUTICAL COMPOSITION CONTAINING THE SAME

(75) Inventors: Zhan Li, Nanjing (CN); Haiyan Huang, Nanjing (CN); Cailian Liu, Nanjing (CN); Lixun Jiang, Nanjing (CN)

(73) Assignee: Nanjing Changao Pharmaceutical Science & Technology Co., Limited, Nanjing (CN)

( * ) Notice: Subject to any disclaimer, the term of this patent is extended or adjusted under 35 U.S.C. 154(b) by 132 days.

(21) Appl. No.: 12/743,898

(22) PCT Filed: Oct. 10, 2008

(86) PCT No.: PCT/CN2008/072646
§ 371 (c)(1), (2), (4) Date: Aug. 24, 2010

(87) PCT Pub. No.: WO2009/089702
PCT Pub. Date: Jul. 23, 2009

(65) Prior Publication Data
US 2010/0311681 A1    Dec. 9, 2010

(30) Foreign Application Priority Data
Jan. 17, 2008 (CN) .......................... 2008 1 0019227

(51) Int. Cl.
*A61K 31/70* (2006.01)
*C07H 19/167* (2006.01)
*C07H 19/173* (2006.01)

(52) U.S. Cl. ...................................... 514/45; 536/27.81

(58) Field of Classification Search .................. None
See application file for complete search history.

(56) References Cited

U.S. PATENT DOCUMENTS 5,068,320 A * 11/1991 Koszalka et al. .......... 536/27.62
5,185,437 A    2/1993 Koszalka et al.

FOREIGN PATENT DOCUMENTS

| CN | 1415622 A | 5/2003 |
|---|---|---|
| CN | 1493301 A | 5/2004 |
| CN | 101147728 A | 3/2008 |
| CN | 101220071 A | 7/2008 |
| WO | 9006312 A1 | 6/1990 |

OTHER PUBLICATIONS (R) Rai et al., "Inhibition of *Mycobacterium tuberculosis*, *Mycobacterium bovis*, and *Mycobacterium avium* by Novel Dideoxy Nucleosides," Journal of Medicinal Chemistry, 50(19), 4766-4774 (Aug. 16, 2007).*
Morris, J. Robins et al, Nucleic Acid-Related Compounds. 88. Efficient Conversions of Ribonucleosides into Their 2, 3-Anhydro, 2 (and 3)-Deoxy, 2, 3-Didexydro-2 ,3-dideoxy, and 2, 3-Dideoxynucleoside Analogs. J. Org. Chem. 1995, vol. 60, No. 24, pp. 7902-7908.

* cited by examiner

*Primary Examiner* — Lawrence E Crane
(74) *Attorney, Agent, or Firm* — Gottlieb, Rackman & Reisman, P.C.

(57) ABSTRACT

A stable 6-methoxy-2',3'-dideoxyguanosine comprises 6-30% water content. It is prepared by absorbing water in 6-methoxy-2',3'-dideoxyguanosine with less than 6% water content at low temperature and certain humidity, or drying 6-methoxy-2',3'-dideoxyguanosine with more than 30% water content. The stable 6-methoxy-2',3'-dideoxyguanosine can be used to prepare medicament composition, and be used to manufacture pharmaceutical for fighting hepatitis B virus or HIV.

11 Claims, 3 Drawing Sheets

STABLE 6-METHOXY-2',3'-DIDEOXYGUANOSINE, METHOD FOR PREPARING THE SAME AND PHARMACEUTICAL COMPOSITION CONTAINING THE SAME

FIELD OF THE APPLICATION

The invention relates to a stable 6-methoxy-2',3'-dideoxyguanosine, a method for preparing the same and a pharmaceutical composition containing the same, which belong to the chemical pharmaceutical field.

BACKGROUND

Hepatitis B is an infectious disease which is caused by hepatitis B virus (HBV), mainly causes hepatic lesions and can cause a variety of organ damages. The harm of the hepatitis B is most serious in various types of existing viral hepatitis, in the acute viral hepatitis, the hepatitis B accounts for about 25% (wt %), and in the chronic hepatitis, the hepatitis B accounts for 80%-90% (wt %). The course of the hepatitis B is prolonged and the hepatitis B is easily transformed into chronic hepatitis, cirrhosis and liver cancer. The endemic areas of the disease spread all over the world, although the HBV infection is prevented by large-area inoculation of hepatitis B vaccines, the prevention and the treatment for current patients with the hepatitis B and HBsAg carriers are still arduous in the following several tens of years.

It is reported in Chinese patent CN1493301A that the 6-methoxy-2',3'-dideoxyguanosine is a nucleoside analogue with anti-HBV activity and can fight against the hepatitis B virus, prevent the production of drug-resistant strains, prevent the liver cancer and fight against lamivudine-resistant virus mutants. In addition, inventors further found that the 6-methoxy-2',3'-dideoxyguanosine plays the role of fighting against the HIV (Human Immunodeficiency Virus) through the experimental study. The 6-methoxy-2',3'-dideoxyguanosine has the following structural formula:

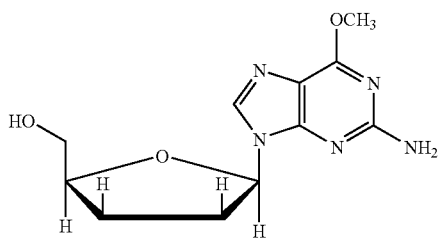

The 6-methoxy-2',3'-dideoxyguanosine can be rapidly metabolized in plasma to 2',3'-dideoxyguanosine (ddG) which is a prodrug of ddG. The ddG can be phosphorylated to an active triphosphate ddGTP in cells, and the DNA replication can be suppressed through the combination with a polymerase, thereby resulting in the stop of the DNA chain synthesis. Although the 6-methoxy-2',3'-dideoxyguanosine can suppress the DNA replication, the DNA polymerase and the polymerase activity of a reverse transcriptase still exist. Meanwhile, compared with a dideoxycytidine triphosphate (ddCTP), although the ddGTP is effective for the chain suspension of the DNA replication, the experimental study shows that the ddGTP can selectively compete with the ddCTP for suppressing the DHBV DNA replication.

Chinese patent CN14156222A and Robins M. J. (J. Org. Chem. 1995, 60(24), 7902-7908), etc. disclose the method for preparing the 6-methoxy-2',3'-dideoxyguanosine. The 6-methoxy-2',3'-dideoxyguanosine obtained by the method disclosed by the forementioned documents is a final product which is finally prepared by the recrystallization method and is in line with the pharmaceutically required purity generally. The water content of the 6-methoxy-2',3'-dideoxyguanosine product prepared by the prior publication documents is not higher than 4% (wt %). However, the inventors found that when the water content of the 6-methoxy-2',3'-dideoxyguanosine obtained by recrystallization in the presence of a variety of solvents and under a variety of conditions (such as temperature and devitrification speed) is lower than 6%, the 6-methoxy-2',3'-dideoxyguanosine is very easy to absorb moisture and be blocked under the general conditions, thereby changing the character thereof and bringing about great inconvenience for transportation, production and pharmaceutical preparations.

CONTENTS OF THE INVENTION

The invention aims at solving the technical problem that when the water content of the current 6-methoxy-2',3'-dideoxyguanosine obtained by the recrystallization is lower than 6% (wt %), the 6-methoxy-2',3'-dideoxyguanosine is very easy to absorb moisture and be blocked under the general conditions, thereby changing the character thereof and bringing about great inconvenience for transportation, production and pharmaceutical preparations, and the invention provides a stable 6-methoxy-2',3'-dideoxyguanosine, a method for preparing the same, a pharmaceutical composition containing the same and an application thereof in the preparation of anti-HBV drugs and anti-HIV drugs.

The water content (weight ratio) of the stable 6-methoxy-2',3'-dideoxyguanosine is 6-30% (wt %) and 15-25% (wt %) preferably.

Generally speaking, when the water content is lower than 6% (wt), the 6-methoxy-2',3'-dideoxyguanosine is very easy to absorb moisture under the general conditions, thereby changing the character and being not conductive to researching and developing pharmaceutical preparations; when the water content is higher than 30% (wt %), the product is easy to be bonded into blocks during the smashing process, thereby being not conductive to researching and developing drugs.

The method for preparing the stable 6-methoxy-2',3'-dideoxyguanosine comprises the following two types:

The first type is as follows: the stable 6-methoxy-2',3'-dideoxyguanosine is obtained by absorbing water of a 6-methoxy-2',3'-dideoxyguanosine solid with less than 6% (wt %) of water content;

The second type is as follows: the stable 6-methoxy-2',3'-dideoxyguanosine is obtained by vacuum drying a 6-methoxy-2',3'-dideoxyguanosine solid with more than 30% (wt %) of water content in the presence of a drying agent.

When the first way is adopted, the environmental temperature when the water is absorbed is lower than 30 degrees centigrade and 0-10 degrees centigrade preferably. The environmental humidity is 20-100% (wt %) and 40%-90% (wt %) preferably. During the process of absorbing the water, the measurement of the water content of the 6-methoxy-2',3'-dideoxyguanosine is carried out till that the water content achieves 6-30% (wt %), and the water content is 15-25% (wt %) preferably.

When the second way is adopted, the temperature during the vacuum drying is lower than 60 degrees centigrade and 20-35 degrees centigrade preferably. The drying agent can be selected from the commonly used drying agents like silicon gel, anhydrous sodium sulfate, anhydrous calcium chloride, phosphorus pentoxide and the like and is the anhydrous calcium chloride preferably. The measurement of the water content of the 6-methoxy-2',3'-dideoxyguanosine is carried out during the drying process till the water content achieves 6-30% (wt %), and the water content is 15-25% (wt %) preferably.

In the method for preparing the stable 6-methoxy-2',3'-dideoxyguanosine according to the invention, the 6-methoxy-2',3'-dideoxyguanosine obtained by any method can be used, such as the 6-methoxy-2',3'-dideoxyguanosine obtained by the preparation method in CN1415622A.

Table 1 is a comparison table, wherein, the 6-methoxy-2',3'-dideoxyguanosine with less than 6% (wt %) of water content is placed in different humidity environments at 5 degrees centigrade for carrying out water-absorbing tests, the products at the corresponding time points are placed in the environment with the temperature of 30 degrees centigrade and the humidity of 90% (wt %) for carrying out the acceleration test inspection, the sampling inspection are carried out at the 15$^{th}$ day, the 30$^{th}$ day and the 60$^{th}$ day respectively, and the inspection indexes comprise the character and the water content.

TABLE 1

| Placement Time | Water Content When Placed in Different Humidity Environments (wt %) | | | Acceleration Test Inspection (Water Content and Character) | | |
|---|---|---|---|---|---|---|
| | Humidity 40% | Humidity 60% | Humidity 90% | 15$^{th}$ Day | 30$^{th}$ Day | 60$^{th}$ Day |
| 0 hour | 2.7 | 2.7 | 2.7 | Aggregate Blocks | Aggregate Blocks | Aggregate Blocks |
| 1 hour | 4.3 | 4.7 | 5.1 | 23.4 Aggregate Blocks | 22.4 Aggregate Blocks | 21.8 Aggregate Blocks |
| 2 hours | 5.4 | 5.7 | 5.8 | 22.9 Aggregate Powder | 22.1 Aggregate Powder | 21.5 Aggregate Powder |
| 14 hours | 8.7 | 8.6 | 8.9 | 22.7 Powder | 22.0 Powder | 21.4 Powder |
| 2 days | 12.6 | 16.3 | 15.9 | 23.0 Powder | 22.5 Powder | 21.6 Powder |
| 3 days | 21.8 | 22.5 | 22.7 | 22.1 Powder | 21.8 Powder | 21.5 Powder |
| 4 days | 22.4 | 23.64 | 22.8 | 22.9 Powder | 21.8 Powder | 21.8 Powder |
| 10 days | 21.8 | 23.5 | 21.9 | 22.0 Powder | 21.7 Powder | 21.9 Powder |

From the Table 1, we can see that, when the water content is lower than 6% (wt %), the product is easy to absorb the water, thereby causing the change of the character; and when the water content is greater than 6% (wt %), the character can be basically kept unchanged.

Therefore, the stable 6-methoxy-2',3'-dideoxyguanosine of the invention is difficult to absorb the moisture under the general conditions and is very stable at room temperature, thereby being capable of keeping good physical properties and providing raw materials with good quality for the production of drugs and pharmaceutical preparations.

The invention further provides a pharmaceutical composition, and the pharmaceutical composition contains the stable 6-methoxy-2',3'-dideoxyguanosine which is taken as an active ingredient and one or a plurality of pharmaceutically acceptable excipients. The pharmaceutical composition can be prepared, according to the conventional pharmaceutical technologies, into tablets or sugar-coated pills, capsules, pastilles, injection, drinkable suspension and other various formulations which are applicable to oral administration or parenteral (intravenous or subcutaneous) application.

The pharmaceutical composition of the invention can be used for treating the hepatitis B and Acquired Immune Deficiency Syndrome. The dosage differs according to different natures and seriousnesses of the diseases, different medication ways and different ages and body weights of patients. The dosage is changed within 1-400 mg per day, and the administration can be carried out by single time or a plurality of times.

The invention overcomes the shortcoming that the current 6-methoxy-2',3'-dideoxyguanosine is easy to absorb the moisture, is very stable at the room temperature and can keep good physical properties and bring about great convenience for the production of drugs and pharmaceutical preparations.

EMBODIMENTS

Figure 1:
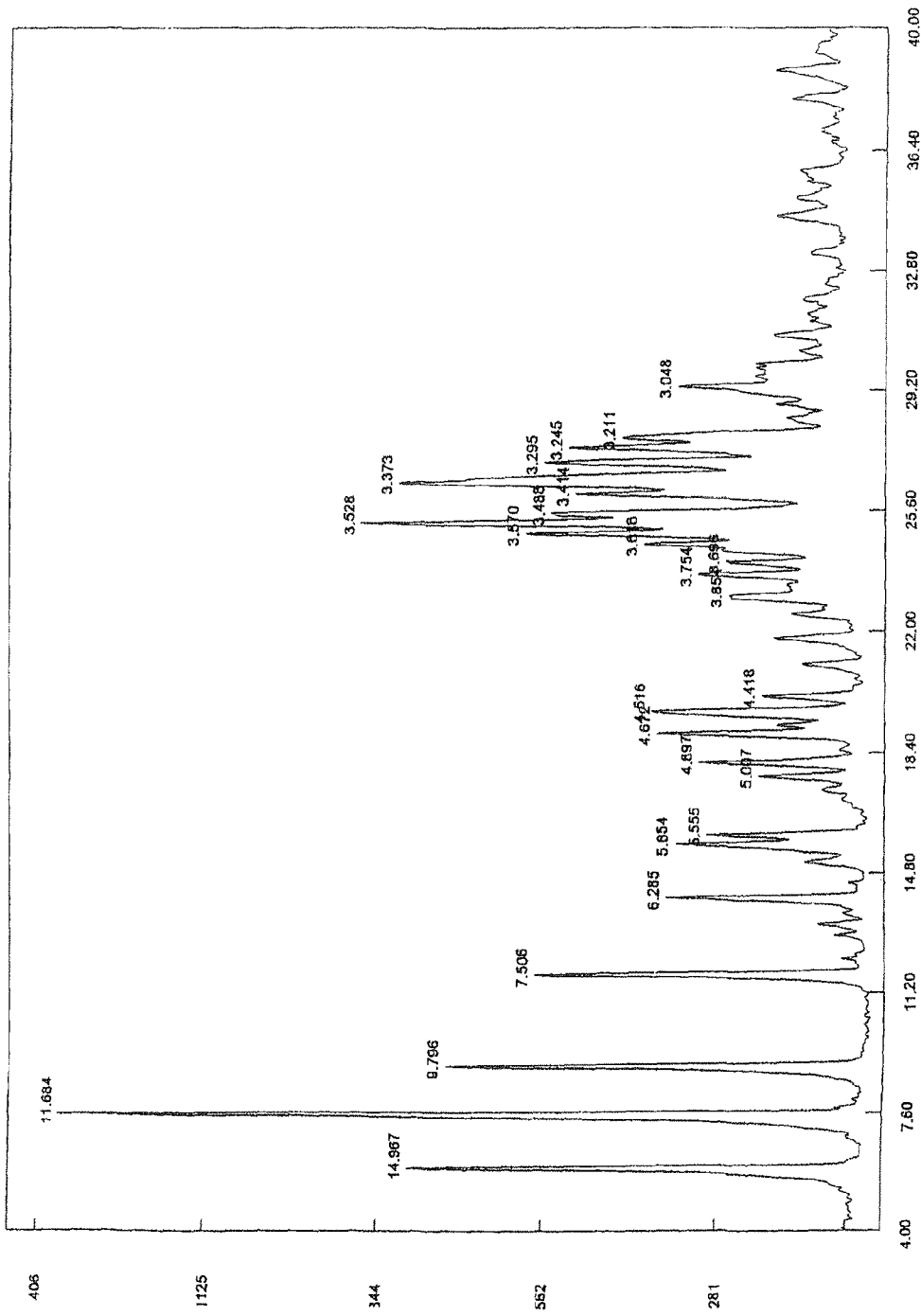
FIG. 1 is an X-ray diffraction spectrum of powder of 6-methoxy-2',3'-dideoxyguanosine with 2.7% (wt %) of water content.

The following uses the embodiments for further describing the invention rather than limiting the invention.

Example 1

1 kg of powder of 6-methoxy-2',3'-dideoxyguanosine with 2.7% (wt %) of water content is laid in a plate flat and placed in the environment with the temperature of 5 degrees centigrade and the humidity of 60% (wt %), is mixed every 1-4 hours, and the required product is obtained after 48 hours.

The water content is measured to be 23.5% (wt %) (by the Karl-Fischer method).

Example 2

0.5 kg of powder of 6-methoxy-2',3'-dideoxyguanosine with 1.5% (wt %) of water content is laid in a plate flat and placed in the environment with the temperature of 15 degrees centigrade and the humidity of 40% (wt %), is mixed every 3-5 hours, and the required product is obtained after 36 hours.

The water content is measured to be 12.5% (wt %) (by the Karl-Fischer method).

Example 3

0.5 kg of powder of 6-methoxy-2',3'-dideoxyguanosine with 3.2% (wt %) of water content is laid in a plate flat and placed in the environment with the temperature of 0 degrees centigrade and the humidity of 90% (wt %), is mixed every 2 hours, and the required product is obtained after 36 hours.

The water content is measured to be 23.2% (wt %) (by the Karl-Fischer method).

Example 4

1.5 kg of powder of 6-methoxy-2',3'-dideoxyguanosine with 60.5% (wt %) of water content is laid in a plate flat and placed in a vacuum drying box, anhydrous calcium chloride is taken as a drying agent, vacuumizing is carried out by a water pump at the temperature of 25 degrees centigrade, decompression drying is further carried out, and the required product is obtained after 48 hours.

The water content is measured to be 22.5% (wt %) (by the Karl-Fischer method).

Example 5

1.0 kg of powder of 6-methoxy-2',3'-dideoxyguanosine with 40.5% (wt %) of water content is laid in a plate flat and placed in a vacuum drying box, phosphorus pentoxide is taken as a drying agent, vacuum decompression drying is carried out at the temperature of 15 degrees centigrade, and the required product is obtained after 38 hours.

The water content is measured to be 18.5% (wt %) (by the Karl-Fischer method).

Example 6

Pharmaceutical Composition

The pharmaceutical composition is used for preparing 1000 capsules, wherein, each capsule contains 40 mg of 6-methoxy-2',3'-dideoxyguanosine based on anhydrides, and the formula thereof is as follows:

| | |
|---|---|
| Compound of Example 4 | 54.2 g |
| Microcrystalline cellulose 102 | 20 g |

-continued

| | |
|---|---|
| Calcium hydrogen phosphate | 20 g |
| Micropowder silicon gel | 1 g |

Figure 2:
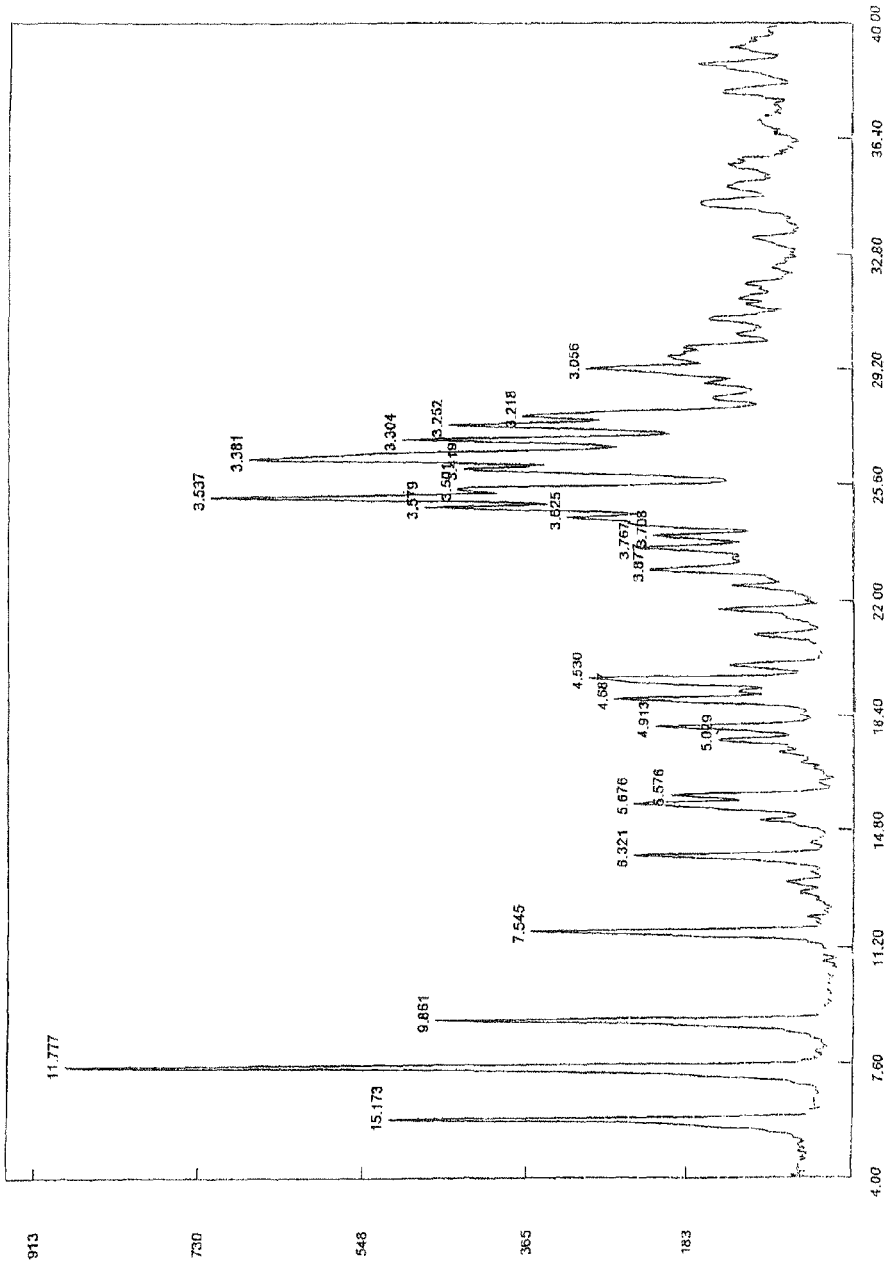
FIG. 2 is an X-ray diffraction spectrum of powder of 6-methoxy-2',3'-dideoxyguanosine with 23.5% (wt %) of water content, wherein, the 6-methoxy-2',3'-dideoxyguanosine is prepared by absorbing water of the 6-methoxy-2',3'-dideoxyguanosine with 2.7% (wt %) of water content at low temperature.
Figure 3:
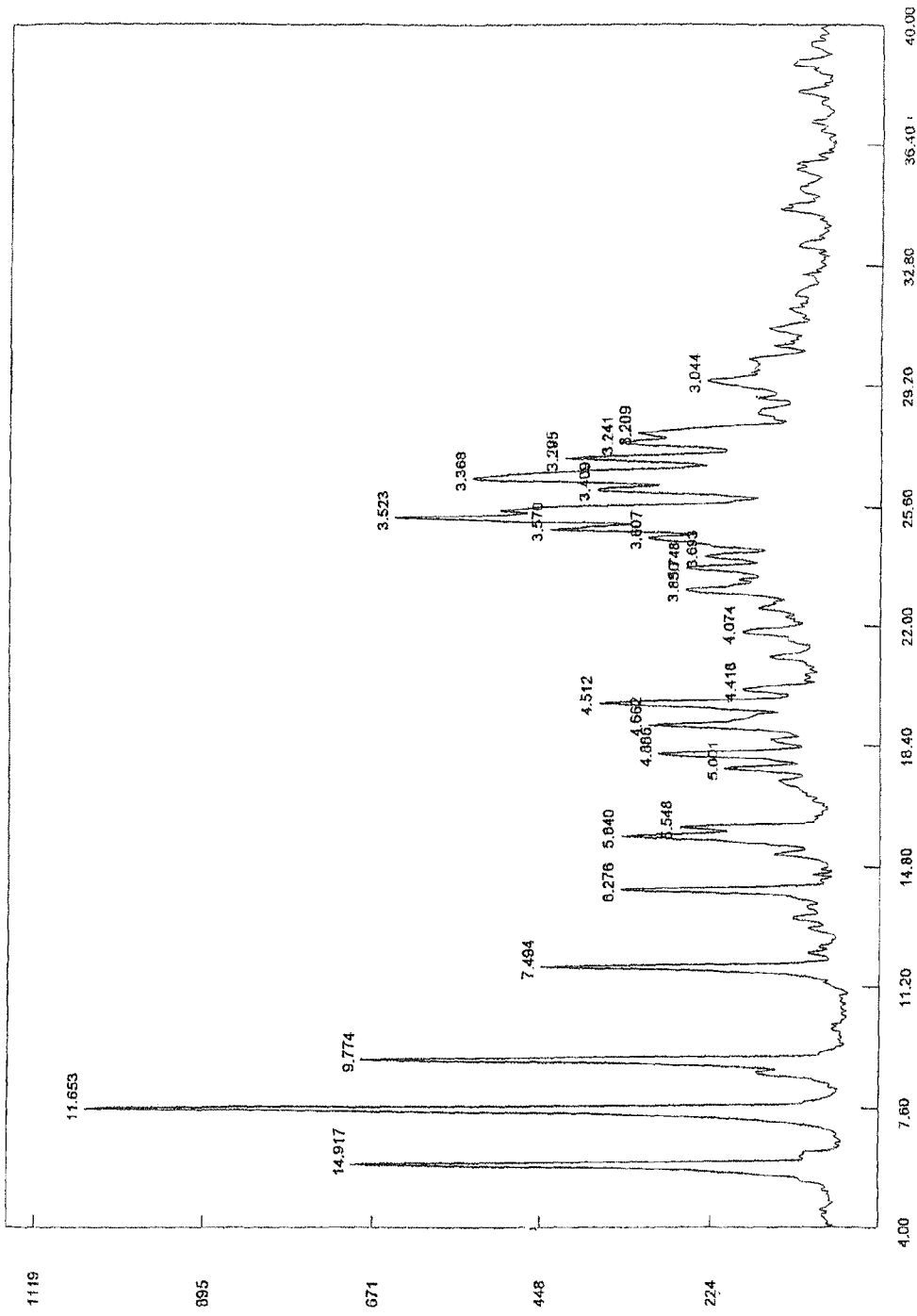
FIG. 3 is an X-ray diffraction spectrum of powder of 6-methoxy-2',3'-dideoxyguanosine with 22.5% (wt %) of water content, wherein, the 6-methoxy-2',3'-dideoxyguanosine is prepared by drying.

With reference to FIG. 1 to FIG. 3, the 6-methoxy-2',3'-dideoxyguanosine with 2.7% (wt %) of water content, the 6-methoxy-2',3'-dideoxyguanosine with 23.5% (wt %) of water content obtained by absorbing water of the 6-methoxy-2',3'-dideoxyguanosine with 2.7% (wt %) of water content at low temperature (5 degrees centigrade), the 6-methoxy-2',3'-dideoxyguanosine with 22.5% (wt %) of water content prepared by drying respectively measure the X-ray diffraction diagrams of powder under the following test conditions: an XTRA X-ray diffraction instrument; start angle: 3; end angle: 40; step length: 0.2; scanning speed: 10; integration time: 0; target: Cu; tube current and tube voltage: 40 KV 40 mA; and slot: 2/4/0.5/0.

The contrast of the spectra shows that the stable 6-methoxy-2',3'-dideoxyguanosine prepared by the above two methods exists in the form of non-crystal water.

What is claimed is:

1. A stable-to-agglomeration 6-methoxy-2',3'-dideoxyguanosine hydrate with a water content in the range of 6-30% (wt %).

2. A stable-to-agglomeration 6-methoxy-2',3'-dideoxyguanosine hydrate with a water content in the range of 15-25% (wt %).

3. A method for preparing the stable-to-agglomeration 6-methoxy-2',3'-dideoxyguanosine of claim 1 or 2, comprising contacting with water a 6-methoxy-2',3'-dideoxyguanosine solid having less than 6% (wt %) of water content.

4. A method for preparing the stable-to-agglomeration 6-methoxy-2',3'-dideoxyguanosine of claim 3, wherein, the environmental temperature is lower than 30 degrees centigrade and the environmental humidity is 20-100% (wt %) when the water is absorbed.

5. A method for preparing the stable-to-agglomeration 6-methoxy-2',3'-dideoxyguanosine of claim 4, wherein, the environmental temperature is 0-10 degrees centigrade and the environmental humidity is 40-90% (wt %) when the water is absorbed.

6. A method for preparing the stable-to-agglomeration 6-methoxy-2',3'-dideoxyguanosine of claim 1 or 2, comprising vacuum drying a 6-methoxy-2',3'-dideoxyguanosine solid with more than 30% (wt %) of water content in the presence of a drying agent.

7. A method for preparing the stable-to-agglomeration 6-methoxy-2',3'-dideoxyguanosine of claim 6, wherein, the temperature for vacuum drying is lower than 60 degrees centigrade.

8. A method for preparing the stable-to-agglomeration 6-methoxy-2',3'-dideoxyguanosine of claim 7, wherein, the temperature for vacuum drying is 20-35 degrees centigrade.

9. A pharmaceutical composition, comprising the stable-to-agglomeration 6-methoxy-2',3'-dideoxyguanosine of claim 1 or 2 as an active ingredient and one or a plurality of pharmaceutically acceptable excipients.

10. A pharmaceutical composition comprising a therapeutically effective quantity of a composition according to claim 1 admixed with at least one pharmaceutically acceptable excipient.

11. A pharmaceutical composition comprising a therapeutically effective quantity of a composition according to claim 2 admixed with at least one pharmaceutically acceptable excipient.

* * * * *